United States Patent [19]

Fried

[11] Patent Number: 5,175,359

[45] Date of Patent: * Dec. 29, 1992

[54] PREPARATION OF ALKOXYALKANOIC ACIDS

[75] Inventor: Herbert E. Fried, Houston, Tex.

[73] Assignee: Shell Oil Company, Houston, Tex.

[ * ] Notice: The portion of the term of this patent subsequent to Nov. 24, 2009 has been disclaimed.

[21] Appl. No.: 752,387

[22] Filed: Aug. 30, 1991

[51] Int. Cl.$^5$ .................... C07C 51/16; C07C 51/235; C07C 51/245; C07C 51/27

[52] U.S. Cl. .................... 562/537; 562/538; 562/540; 562/587

[58] Field of Search ............... 562/538, 537, 587, 540

[56] References Cited

PUBLICATIONS

Anelli et al. J. Organic Chem. 52(12) 2559 (1987).
Yamaguchi et al. Pure and Applied Chem. 62(2),217 (1990).
Inokuchi et al. J. Organic Chem. 55(1990), 462.

Primary Examiner—José G. Dees
Assistant Examiner—Joseph M. Conrad, III
Attorney, Agent, or Firm—Pamela J. McCollough

[57] ABSTRACT

A process for the preparation of an alkoxyalkanoic acid of the formula $$RO(CH_2CHR'O)_nCH_2CO_2H$$

wherein R is an alkyl group of from 1 to about 22 carbon atoms, R' is hydrogen or methyl or mixtures thereof (on the individual molecule) and n is an integer of from 1 to about 20, which comprises reacting the corresponding alkoxyalkanol with a solubilized stable free radical nitroxide having the formula:

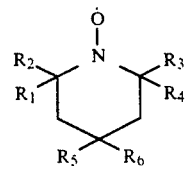

wherein each of $R_1$, $R_2$, $R_3$ and $R_4$ is an alkyl, aryl or heteroatom substituted alkyl group having 1 to about 15 carbon atoms and each of $R_5$ and $R_6$ is alkyl, hydrogen, aryl or a substituted heteroatom, a $NO_x$-generating compound selected from the group consisting of an alkali metal nitrosodisulfonate, nitric acid, nitrous acid and mixtures thereof, and a chloride ion-containing compound in the presence of an oxidant at a temperature in the range of from about 0° C. to about 100° C. and thereafter separating out the alkoxyalkanoic acid.

18 Claims, No Drawings

PREPARATION OF ALKOXYALKANOIC ACIDS

FIELD OF THE INVENTION

This invention relates to a process for the preparation of alkoxyalkanoic acids by the oxidation of the corresponding alkoxyalkanols in the presence of a stable free radical nitroxide, a $NO_x$-generating compound, a chloride ion-containing compound and an oxidant.

BACKGROUND OF THE INVENTION

Alkoxyalkanoic acids are useful as anionic detergents. These acids, being composed of only the elements C, H and O, do not pose the environmental problems that other detergents containing heteroatoms such as N, S, and P pose. Commercially, the alkoxyalkanoic acids are prepared in a two-step process of first reacting an alkoxyalkanol with sodium and then reacting the resultant alkoxide with the sodium salt of chloroacetic acid.

It is also known to convert alkoxyalkanols such as methyl carbitol to the corresponding carboxylic acids by oxidizing them with nitric acid. However, not all of the nitric acid can be separated by distillation, and the reaction product contains nitric acid, which is corrosive and therefore undesirable. In addition, cleavage of the ether linkages occurs to a large degree during this process.

Japanese Patent No. 50-96516. issued Jul. 31, 1975. discloses a process for the preparation of carboxylic acid salts by the liquid phase dehydrogenation of alcohols with caustic alkali in the presence of precious metal catalysts, including palladium. This process uses a relatively high temperature, 100° C.–270° C. These high temperatures can degrade the ether linkages especially in the highly ethoxylated alcohols.

It is known to use nitroxyl radicals/oxoammonium salts in the oxidation of primary alcohols to produce aldehydes and acids and secondary alcohols to ketones. *Journal of Organic Chemistry*, vol. 52 (12), pp. 2559-2562; *Pure and Applied Chemistry*, vol. 62(2), 1990, pp. 217-222; *Journal of Organic Chemistry*, vol. 55, 1990, pp. 462-466. The primary products produced in these processes are aldehydes and the stoichiometrically consumed oxidant is hypochlorite.

It is generally more difficult to oxidize alkoxyalkanols than alkanols as it is difficult to oxidize alkoxyalkanols without splitting the molecular chain at the ether linkage and thereby produce a large proportion of undesired by-product.

OBJECTS OF THE INVENTION

It is therefore an object of this invention to produce alkoxyalkanoic acids in high yields and with high selectivities from alkoxyalkanols without producing large amounts of other products such as aldehydes, esters and cleavage products.

It has been found that alkoxyalkanoic acids can be produced in high yields and with high selectivities by using catalytic amounts of a stable free radical nitroxide, a $NO_x$-generating compound selected from the group consisting of an alkali metal nitrosodisulfonate, nitric acid, nitrous acid and mixtures thereof, a chloride ion-containing compound and an oxidant.

SUMMARY OF THE INVENTION

This invention relates to a process for the preparation of an alkoxyalkanoic acid of the formula $$RO(CH_2CHR'O)_nCH_2CO_2H$$

wherein R is an alkyl group of from 1 to about 22 carbon atoms R' is hydrogen or methyl or mixtures thereof (on the individual molecule) and n is an integer of from 1 to about 12 which comprises reacting the corresponding alkoxyalkanol with a solubilized stable free radical nitroxide having the formula:

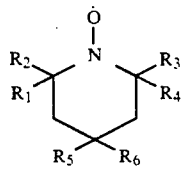

wherein each of $R_1$, $R_2$, $R_3$ and $R_4$ is an alkyl, aryl or heteroatom substituted alkyl group having 1 to about 15 carbon atoms and each of $R_5$ and $R_6$ is alkyl, hydrogen, aryl or a substituted heteroatom, a $NO_x$-generating compound selected from the group consisting of an alkali metal nitrosodisulfonate, nitric acid, nitrous acid and mixtures thereof, and a chloride ion-containing compound in the presence of an oxidant at a temperature in the range of from about 0° C. to about 100° C. and thereafter separating out the alkoxy alkanoic acid.

DESCRIPTION OF THE PREFERRED EMBODIMENTS

The present process converts alkoxyalkanols of the formula $$RO(CH_2CHR'O)_nCH_2CH_2OH \qquad (I)$$

wherein R is an alkyl group, preferably 1 to about 22; more preferably about 11 to about 18 carbon atoms, R' is hydrogen or methyl or mixtures thereof (on the individual molecule) and n represents the average number of oxyalkylene groups and is an integer of from 1 to about 20, preferably of from about 2 to about 9, to the corresponding alkoxyalkanoic acids of the formula:

$$RO(CH_2CHR'O)_nCH_2CO_2H \qquad (II)$$

by contacting the alkoxyalkanol with a solubilized stable free radical nitroxide and a $NO_x$-generating compound selected from the group consisting of an alkali metal nitrosodisulfonate, nitric acid and mixtures thereof, in the presence of an oxidant at a temperature in the range of from about 0° C. to about 100° C. and thereafter separating out the alkoxyalkanoic acid. The R group in the above formula I can be substituted with any substituent which does not interefere with the oxidation of the hydroxy group. Such substituents include $-OR''$, $-CH_3$, $-COOH$, $CONH_2$ and $COOR''$ wherein R'' is an alkyl or aryl group. The process of the instant invention is particularly suited to detergent range ethoxylated, or propoxylated alcohols with alkyl chains (R) of about 8 to about 20, preferably of about 11 to about 18 carbon atoms. The R' groups on an individual molecule can be hydrogen, methyl or mixtures thereof. For example, straight ethoxylated, straight propoxylated and mixed ethoxylated-propoxylated detergent alcohols are commercially available.

The number of such alkoxylate groups, (CH$_2$CHR'O), range from 1 to about 20. Commercially, detergent range ethoxylate alcohols are available with an average of 3, 7, 9 and 12 ethoxylate units per molecule. Others can be readily prepared. In a preferred embodiment, the starting alkoxyalkanol is ethoxylated alcohol which has had the unreacted alcohols and lower ethoethoxylates topped off in order to give an ethoxylate having about four ethylene oxide units per molecule.

The term "stable free radical nitroxide" as used herein shall mean a free radical nitroxide that can be prepared by conventional chemical methods and will exist long enough to be used in a subsequent chemical reaction or examined in a static system by normal methods of spectroscopy. Generally, the stable free radical nitroxides of the present invention have a half life of at least one year. The term "stable free radical" shall also be understood to include the precursor to a stable free radical from which the stable free radical may be produced in situ.

The stable free radical nitroxides, as used in the present process, are precursors to catalysts, i.e., oxoammonium salts, active for the oxidation of alkoxyalkanols to the corresponding acids. These catalysts are generated in situ by the oxidation of a stable free radical nitroxide to an oxoammonium salt with an oxygen-containing oxidant. The stable free radical nitroxide can be obtained by the oxidation of secondary amines or hydroxylamines.

The stable free radical nitroxides which are suitable for use in the instant invention have the formula:

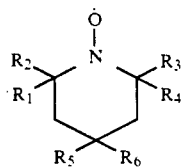

wherein each of R$_1$, R$_2$, R$_3$ and R$_4$ is an alkyl, aryl or heteroatom substituted alkyl group having 1 to about 15 carbon atoms and no hydrogen is bound to the remaining valences on the carbon atoms bound to the nitrogen, and each of R$_5$ and R$_6$ is alkyl, hydrogen, aryl or a substituted heteroatom. As used herein, the term "alkyl" is meant to include cycloalkyl. The alkyl (or heteroatom substituted) groups R$_1$-R$_4$ may be the same or different, and preferably contain 1 to 15 carbon atoms. Preferably, R$_1$-R$_4$ are methyl, ethyl, or propyl groups. In addition to hydrogen, the heteroatom substituents may include, halogen, oxygen, nitrogen and the like. Preferably, one of R$_5$ and R$_6$ is hydrogen with the other one being a substituted heteroatom which does not interfere with the reaction. Suitable substituted heteroatoms include —OR,

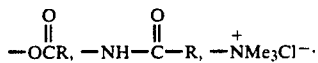

—O—SO$_3$H, —O— polymer and the like.

In a preferred embodiment, the nitroxide is selected from the group consisting of 2,2,6,6-tetramethyl-piperidine-1-oxyl, 4-hydroxy-2,2,6,6-tetramethyl-piperidine-1-oxyl, 4-oxo-2,2,6,6-tetramethyl-piperidine-1-oxyl, 2,2,6,6-tetramethyl-piperidine-1-oxyl-4-sulfate, 4-alkoxy-2,2,6,6-tetramethyl-piperidine-1-oxyl and mixtures thereof, with 2,2,6,6-tetra-methyl-piperidine-1-oxyl, 2,2,6,6-tetramethyl-piperidine-1-oxyl-4-sulfate, and 4-alkoxy-2,2,6,6-tetramethyl-piperidine-1-oxyl being particularly preferred.

The NO$_x$-generating compound in the present process is typically selected from the group consisting of an alkali metal nitrosodisulfonate, nitric acid, nitrous acid and mixtures thereof. However, any compound which serves to generate NO$_x$ during the course of the reaction and which does not interfere with the reaction would be suitable.

The alkali metal nitrosodisulfonate suitable for use as a NO$_x$-generating compound can be any alkali metal nitrosodisulfonate although potassium nitrosodisulfonate is preferred. As used herein, the term "alkali metal" is used as a descriptor of the elements Group IA of the Periodic Table of the Elements (Li, Na, K, Rb, Cs, Fr). The alkali metal nitrosodisulfonate is typically dissolved in water prior to being added to the reaction mixture although it can be added as a solid after all of the other reactants have been added.

The nitric acid suitable for use as a NO$_x$-generating compound in the present invention typically has a concentration in the range of from about 50 percent to about 100 percent, preferably about 70 percent. Generally, an amount of nitric acid in the range of from about 5 mole percent to about 100 mole percent, basis the number of moles of starting alkoxyalkanol is used. If excess nitric acid is used and the reaction mixture becomes too acidic, the reaction stops. The nitric acid is typically added to the reaction mixture after all of the other reactants have been added. While not wishing to be bound by any particular theory, it is believed that nitrogen oxides (NO$_x$) are generated in the reaction and are the active species in the reaction.

The chloride ion in the present invention can be any ionic chloride which is in a soluble form. The presence of chloride ion is critical to the instant process as it dramatically increase the rate of the reaction. The chloride ion is suitably introduced into the process as a quaternary alkyl chloride such as, for example, tricaprylylmethyl ammonium chloride, a tetraalkyl chloride such as, for example, tetramethyl ammonium chloride, an alkali metal chloride such as for example, sodium chloride, potassium chloride, lithium chloride, calcium chloride and the like. In a preferred embodiment, the chloride ion-containing compound is selected from the group consisting of tricaprylylmethyl ammonium chloride, sodium chloride, potassium chloride and mixtures thereof, with tricaprylylmethyl ammonium chloride being particularly preferred.

The oxidants suitable for use in the instant invention are those compounds which are capable of oxidizing the stable free radical nitroxide to the oxoammonium salt. Suitable oxidants include oxygen or an oxygen-containing gas such as air. Whereas pure oxygen can is preferred to accomplish the desired conversion, dilution of the oxygen with an inert gas such as nitrogen, helium, argon, or other similar gas is also suitable. While air can be used as the oxidant, the reaction rate is much slower. For purposes of increasing the reaction rate, higher O$_2$ pressures such as, for example, 1000 psi can be utilized. In a preferred embodiment, pure oxygen is used as the oxidant and it is bubbled into the reaction solution. In another embodiment, air can be bubbled initially through the reaction solution.

The reaction in the instant invention can be carried out in the presence or absence of a solvent. As the reaction rate increases when no solvent is utilized, the reaction is preferably carried out without solvent. When the reaction is carried out in the presence of a solvent, the solvent is generally a solvent in which the alkoxyalkanol is readily soluble. Solvents which are most suitable are those which are inert in the reaction. The solvent may be added to the reaction mixture, or alternatively, the nitroxide may be dissolved in the solvent prior to addition of the nitroxide to the reaction medium. The solvent is typically selected from the group consisting of acetonitrile, ethyl acetate, tertiary alcohols such as tertiary butyl alcohol, dichloromethane, chlorobenzene and mixtures thereof. In a preferred embodiment, the solvent is selected from tert-butyl alcohol and acetonitrile. The amount of solvent utilized in the process is typically in the range of from about 20:1 to about 0.5:1, preferably from about 10:1 to about 5:1, basis the weight of the starting alkoxyalkanol.

The amounts and concentrations of the reactants utilized in the process of the instant invention can vary within wide ranges. The amount of stable free radical nitroxide is typically in the range of from about 1 mole percent to about 50 mole percent, preferably from about 5 mole percent to about 30 mole percent, basis the number of moles of starting alkoxyalkanol. Generally, the amount of $NO_x$-generating compound is in the range of from about 25 mole percent to about 50 mole percent, basis the number of moles of starting alkoxyalkanol. When an alkali metal nitrosodisulfonate is utilized as the $NO_x$-generating compound, the amount used will typically be in the range of from about 1 mole percent to about 35 mole percent, preferably from about 10 mole percent to about 20 mole percent, basis the number of moles of the starting alkoxyalkanol. When nitric acid is utilized, the concentration will typically be in the range of from about 5 mole percent to about 100 mole percent, preferably from about 25 mole percent to about 50 mole percent, basis the starting alkoxyalkanol. Generally, the chloride ion-containing compound is present in an amount sufficient to catalyze the reaction. Typically, the amount of chloride ion-containing compound is about 3 mole percent basis the starting alkoxyalkanol.

The process of the present invention is typically conducted under mild conditions, with good results being obtained using a temperature in the range of from about 0° C. to about 100° C. preferably about 20° C. to about 70° C., and more preferably about 40° C. to about 60° C. Reaction pressures are not critical although higher pressures result in increased reaction rates. Pressures in the range of from about atmospheric pressure up to about 1000 psig can be employed with good results.

The process of the instant invention can be carried out either batchwise or continuously, using a stirrer equipped reactor or other well known contacting technique to achieve adequate mixing. Preferred reaction conditions, e.g., temperature, pressure, flow rates, etc., vary somewhat depending on the specific nitroxide utilized and on the concentration of the nitroxide.

The process of the instant invention can be carried out in a variety of ways. For example, 0.032 moles of alkoxyalkanol, 0.006 moles percent by weight of the nitroxide, and 0.001 moles of chloride ion-containing compound may be added to the reaction vessel, followed by the addition of 0.016 moles of $NO_x$-generating compound and $O_2$. Alternatively, the alkoxyalkanol, the nitroxide, the $NO_x$-generating compound, and the chloride ion-containing compound and the oxidant may be added simultaneously to the reaction vessel and allowed to reach equilibrium. In a preferred embodiment, the reaction is carried out by adding the alkoxyalkanol, the nitroxide, and the chloride ion-containing compound together with the solvent, if one is used, and thereafter adding the $NO_x$-generating compound and bubbling an oxidizing gas through the mixture. Following the reaction, the product may be separated from the reaction mixture using conventional procedures such as extraction using a suitable extraction solvent such as, for example, ethyl acetate; evaporation wherein the solvent is stripped from the reaction mixture by using heat or vacuum. Phase separation of the acidified solution takes place at 100° C. with water. The reaction product can be purified by a number of conventional means such as high temperature water washing or extraction.

Depending upon process conditions and the nitroxide used, the yields of alkoxyalkanoic acid obtained by this invention can be greater than about 98% of starting material being converted. The products produced by the instant process can be used in a variety of detergent applications. For example, light duty dishwashing liquids, shampoos and heavy duty laundry liquids or powders.

The ranges and limitations provided in the instant specification and claims are those which are believed to particularly point out and distinctly claim the present invention. It is, however, understood that other ranges and limitations which perform substantially the same function in the same or substantially the same manner to obtain the same or substantially the same result are intended to be within the scope of the instant invention as defined by the instant specification and claims.

The process of this invention will be further described by the following embodiments which are provided for illustration and are not to be construed as limiting the invention.

ILLUSTRATIVE EMBODIMENTS

In the following examples, the starting alkoxyalkanol was a NEODOL ® Ethoxylate 23-3T alcohol which was prepared by ethoxylating a mixture of $C_{12}$ and $C_{13}$ substantially straight chain alcohols ($C_{12}$ : $C_{13}$ ~40:60) to an ethoxylate alcohol having about 3 ethylene oxide units per molecule and then topping off the unreacted alcohols and lower ethoxylates so that the final product has about three ethylene oxide units per molecule.

EXAMPLE 1

12 Grams of NEODOL ® Ethoxylate 23-3T, gram of 2,2,6,6-tetramethyl-piperidine-1-oxyl, 50 milliliters of tertiary butyl alcohol, 2 grams of water, 0.5 grams of Aliquat 336 (tricaprylylmethyl ammonium chloride) were charged to a 100 milliliter round bottomed flask. To this mixture was added 1 gram of 70% nitric acid and $O_2$. The reaction was held at room temperature over a 16 hour period. The results are presented in Table I.

EXAMPLE 2

12 Grams of NEODOL ® Ethoxylate 23-3T, 1 gram of 2,2,6,6-tetramethyl-piperidine-1-oxyl, 50 milliliters of acetonitrile, 1 gram of water, 2 grams of potassium nitrosodisulfonate and 0.1 gram of sodium chloride were charged to a 100 milliliter round bottomed flask. The reaction was held room temperature over a 16 hour period. The results are presented in Table I.

EXAMPLE 3

12 Grams of NEODOL ® Ethoxylate 23-3T, 1 gram of 2,2,6,6-tetra-methyl-piperidine-1-oxyl, 50 milliliters of acetonitrile, 1 gram of water, and 0.5 grams of Aliquat 336 (tricaprylylmethyl ammonium chloride) were charged to a 100 milliliter round bottomed flask. To this mixture was added 2 grams of potassium nitrosodisulfonate and $O_2$. The reaction was held at room temperature over a 16 hour period. The results are presented in Table I.

EXAMPLE 4

12 Grams of NEODOL ® Ethoxylate 23-3T, 1 gram of 2,2,6,6-tetra-methyl-piperidine-1-oxyl, 50 milliliters of tertiary butyl alcohol, 1 gram of water, and 2 grams of potassium nitrosodisulfonate and 0.5 grams of Aliquat 336 (tricaprylylmethyl ammonium chloride) were charged to a 100 milliliter round bottomed flask. The temperature was held at room temperature over a 16 hour period. The results are presented in Table I.

COMPARATIVE EXAMPLE A

Comparative Example A was carried out in a manner similar to Example 1 except that no chloride ion-containing compound was used. The results are presented in Table I.

COMPARATIVE EXAMPLE B

Comparative Example B was carried out in a manner similar to Example 4 except that no chloride ion-containing compound was used. The results are presented in Table 1.

TABLE I

| Oxidation Of Alkoxyalkanols to Alkoxyalkanoic Acids | | | | |
|---|---|---|---|---|
| | % Conversion | % Sel. Acids | % Sel. Esters + Heavies | % Sel. Aldehydes |
| Example 1 | 99.5 | 99 | <.2 | <1 |
| Example 2 | 71 | 97 | 3 | <1 |
| Example 3 | 87 | 99 | 1.0 | <1 |
| Example 4 | 50.4 | 98.6 | 1.4 | <1 |
| Comparative Example A | 1 | 0 | 0 | 100 |
| Comparative Example B | 21 | 57 | <.2 | 43 |

What is claimed is:

1. A process for the preparation of an alkoxyalkanoic acid of the formula

wherein R is an alkyl group of from 1 to about 22 carbon atoms, R' is hydrogen or methyl or mixtures thereof (on the individual molecule) and n is an integer of from 1 to about 20, which comprises reacting the corresponding alkoxyalkanol with a solubilized stable free radical nitroxide having the formula:

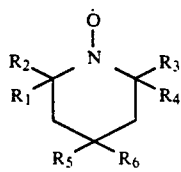

wherein each of $R_1$, $R_2$, $R_3$ and $R_4$ is an alkyl, aryl or heteroatom substituted alkyl group having 1 to about 15 carbon atoms and each of $R_5$ and $R_6$ is alkyl, hydrogen, aryl or a substituted heteroatom, a $NO_x$-generating compound selected from the group consisting of an alkali metal nitrosodisulfonate, nitric acid, nitrous acid and mixtures thereof, and a chloride ion-containing compound in the presence of an oxidant at a temperature in the range of from about 0° C. to about 100° C. and thereafter separating out the alkoxyalkanoic acid.

2. The process of claim 1 wherein the solubilized stable free radical nitroxide is selected from the group consisting of 2,2,6,6-tetra-methyl-piperidine-1-oxyl, 4-hydroxy-2,2,6,6-tetramethyl-piperidine-1-oxyl, 4-oxo-2,2,6,6-tetramethyl-piperidine-1-oxyl, 2,2,6,6-tetramethyl-piperidine-1-oxyl-4-sulfate, 4-alkoxy-2,2,6,6-tetramethyl-piperidine-1-oxyl and mixtures thereof.

3. The process of claim 2 wherein the solubilized stable free radical nitroxide is selected from the group consisting of 2,2,6,6-tetramethyl-piperidine-1-oxyl, 2,2,6,6-tetramethyl-piperidine-1-oxyl-4-sulfate, 4-alkoxy-2,2,6,6-tetramethyl-piperidine-1-oxyl and mixtures thereof.

4. The process of claim 1 wherein said $NO_x$-generating compound is an alkali metal nitrosodisulfonate selected from the group consisting of potassium nitrosodisulfonate, sodium nitrosodisulfonate, and mixtures thereof.

5. The process of claim 4 wherein said $NO_x$-generating compound is an alkali metal nitrosodisulfonate.

6. The process of claim 5 wherein said alkali metal nitrosodisulfonate is potassium nitrosodisulfonate.

7. The process of claim 1 wherein said $NO_x$-generating compound is nitric acid.

8. The process of claim 7 wherein said nitric acid has a concentration in the range of from about 5 mole percent to about 100 mole percent, basis the starting alkoxyalkanol.

9. The process of claim 1 wherein said chloride ion-containing compound is selected from the group consisting of a quaternary alkyl chloride, a tetraalkyl chloride, an alkali metal chloride and mixtures thereof.

10. The process of claim 9 wherein said chloride ion-containing compound is selected from the group consisting of tricaprylylmethyl ammonium chloride, sodium chloride, potassium chloride and mixtures thereof.

11. The process of claim wherein said alkoxyalkanol is contacted with said solubilized stable free radical nitroxide and said chloride ion-containing compound, followed by the addition thereto of said $NO_x$-generating compound and said oxidant.

12. The process of claim 11 wherein the amount of solubilized stable free radical nitroxide is in the range of from about 1 mole percent to about 25 mole percent, basis the number of moles of the alkoxyalkanol.

13. The process of claim 12 wherein the amount of solubilized stable free radical nitroxide is in the range of from about 5 mole percent to about 20 mole percent, basis the number of moles of the alkoxyalkanol.

14. The process of claim 1 wherein said oxidant is an oxygen-containing gas.

15. The process of claim 14 wherein said oxygen containing gas is selected from the group consisting of pure oxygen and air.

16. The process of claim 15 wherein said oxygen-containing gas is pure oxygen.

17. The process of claim 1 wherein said process is carried out at a temperature in the range of from about 20° C. to about 70° C. and at atmospheric pressure.

18. The process of claim 17 wherein said process is carried out at a temperature in the range of from about 40° C. to about 60° C. and at atmospheric pressure.

* * * * *